United States Patent
Li et al.

(10) Patent No.: US 10,124,133 B2
(45) Date of Patent: Nov. 13, 2018

(54) ELECTRONIC FLOW MONITOR, CONTROL METHOD AND ANESTHESIA MACHINE

(75) Inventors: Hua Li, Shenzhen (CN); Honglei Li, Shenzhen (CN); Sheng Wang, Shenzhen (CN); Li Han, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1156 days.

(21) Appl. No.: 14/235,771

(22) PCT Filed: Jun. 7, 2012
(Under 37 CFR 1.47)

(86) PCT No.: PCT/CN2012/076580
§ 371 (c)(1),
(2), (4) Date: Jul. 8, 2014

(87) PCT Pub. No.: WO2013/016976
PCT Pub. Date: Feb. 7, 2013

(65) Prior Publication Data
US 2016/0001023 A1    Jan. 7, 2016

(30) Foreign Application Priority Data
Aug. 1, 2011 (CN) .......................... 2011 1 0218006

(51) Int. Cl.
*A61M 16/00* (2006.01)
*A61M 16/12* (2006.01)
(Continued)

(52) U.S. Cl.
CPC ...... *A61M 16/0003* (2014.02); *A61M 16/104* (2013.01); *A61M 16/1005* (2014.02);
(Continued)

(58) Field of Classification Search
CPC .......... A61M 16/0003; A61M 16/1005; A61M 16/1015; A61M 16/204; A61M 16/104;
(Continued)

(56) References Cited

U.S. PATENT DOCUMENTS

| 4,442,856 A | 4/1984 | Betz |
| 6,024,087 A | 2/2000 | Kersey et al. |

FOREIGN PATENT DOCUMENTS

| CN | 2290351 Y | 9/1998 |
| CN | 101496925 A | 8/2009 |
| CN | 201692468 U | 1/2011 |

OTHER PUBLICATIONS

CN2290351Y machine translation of specifcation Jan. 11, 2017.*
CN201692468U machine translation of specifcation Jan. 11, 2017.*

* cited by examiner

*Primary Examiner* — Gregory Anderson
*Assistant Examiner* — Elliot S Ruddie
(74) *Attorney, Agent, or Firm* — Polsinelli LLP; Kory D. Christensen

(57) ABSTRACT

An electronic flow monitor, a control method and an anesthesia machine. The electronic flow controller can comprise a control module, an oxygen gas branch for delivering oxygen gas, an equilibrium gas branch for delivering equilibrium gas, and a gas mixing branch for mixing the oxygen gas and the equilibrium gas. The control module can meter an oxygen gas flow and an equilibrium gas flow through flow sensors. A first flow controller can be disposed in the oxygen gas branch, and a second flow controller can be disposed in the equilibrium gas branch. The first flow controller may be used to regulate the gas flow in the oxygen gas branch between zero and a maximum value and the
(Continued)

second flow controller may be used to regulate the gas flow in the equilibrium gas branch between zero and a maximum value.

18 Claims, 4 Drawing Sheets

(51) Int. Cl.
*A61M 16/10* (2006.01)
*A61M 16/20* (2006.01)
*A61M 16/22* (2006.01)

(52) U.S. Cl.
CPC ........ *A61M 16/1015* (2014.02); *A61M 16/12* (2013.01); *A61M 16/204* (2014.02); *A61M 16/0051* (2013.01); *A61M 16/022* (2017.08); *A61M 16/22* (2013.01); *A61M 2016/0027* (2013.01); *A61M 2016/0039* (2013.01); *A61M 2202/0208* (2013.01); *A61M 2202/0283* (2013.01); *A61M 2205/3334* (2013.01)

(58) Field of Classification Search
CPC .. A61M 16/12; A61M 16/0051; A61M 16/22; A61M 2016/0027; A61M 2016/0039; A61M 2202/0208; A61M 2202/0283; A61M 2205/3334; A61M 2016/1035; A61M 16/20; A61M 16/201; A61M 16/202; A61M 16/203; A61M 2016/0033
USPC ....................................... 128/203.12, 203.14
See application file for complete search history.

ELECTRONIC FLOW MONITOR, CONTROL METHOD AND ANESTHESIA MACHINE

TECHNICAL FIELD

This disclosure generally relates to electronic flow monitors and anesthesia machines using the same.

BACKGROUND

FIG. 1 shows an anesthesia machine that can control the anesthetic inhalation and mechanical ventilation for a patient during surgery. The gas inhaled by the patient can be circulated in a closed-loop breathing circuit equipped with a carbon dioxide absorber. The carbon dioxide absorber may contain dry soda lime for absorbing the carbon dioxide exhaled by the patient. Due to oxygen consumption by the patient and undesirable leakage, the gas circulated in the breathing circuit may decrease gradually. Thus the anesthesia machine often employs an independent channel for constantly supplementing gas into the breathing circuit. The gas supplemented through this independent channel can be called fresh gas.

The fresh gas may be formed in two steps: different flows of oxygen and equilibrium gas (such as air or nitrous oxide) may first be mixed in a flow monitor; the mixed gas outputted from the flow monitor may then be passed through an anesthetic volatilization device (containing some anesthetic) to form the fresh gas to be delivered into the breathing circuit.

The flow monitor may mechanically and/or electronically regulate flows of the oxygen and the equilibrium gas.

For the mechanical regulation, a mechanical needle valve can be used by a user for such flow regulation, and a flow sensor or a mechanical rotameter can further be used for monitoring the flows of the oxygen and the equilibrium gas. This mechanical regulation mode can be implemented with simple systems with low cost and high reliability, while it may not be adequate in terms of automation. In addition, the user may need to manually calculate the desired flows of the oxygen and the equilibrium gas so as to obtain desired oxygen concentration and total flow. Consequently, the mechanical mode is generally employed in low and medium-grade anesthesia machines.

For the electronic regulation, a user may need to input desired oxygen concentration and total flow, and then the regulation system can monitor respective gas flows to meet a regulation target set by the user. This electronic regulation mode thus can have high automation, simple operation and high accuracy, but the systems used may be complicated with high cost. As a result, the electronic mode is generally employed in middle and high-grade anesthesia machines.

Flow monitors using electronic regulation mode are often called as electronic flow monitors.

FIG. 2 shows an existing electronic flow monitor, which can include an oxygen branch 2, an oxygen bypass 1, a nitrous oxide branch 3 and an air branch 4.

The oxygen branch 2 may be arranged with an on-off controller 7 (e.g., gate valve), a flow control valve 8, a pressure sensor 10, a flow sensor 9 and a one-way valve 11.

The nitrous oxide branch 3 and the air branch 4 may be respectively equipped with an on-off controller 7, where at most one of these two on-off controllers can be in an "on" state at any given instant. A shared gas branch 5 can also be arranged for the nitrous oxide branch 3 and the air branch 4, and the shared gas branch 5 can be equipped with a flow control valve 8, a pressure sensor 10, a flow sensor 9 and a one-way valve 11.

A gas mixing branch 6 may include a pressure sensor 10. The oxygen bypass 1 may be equipped with a mechanical needle valve 12 and an on-off controller 7. This on-off controller 7 is in an "on" state (i.e., open) when there is no power supply. This is different from the rest of the on-off controllers used in the electronic flow monitor, which would be in an "off" state (i.e., closed) when there is no power supply. In this way, the oxygen bypass 1 can be switched to an "on/open" state to supply pure oxygen to the patient in case the power is lost. The mechanical needle valve 12 can be used for regulating gas flow, and the on-off controller 7 can prevent any oxygen from flowing through the oxygen bypass 1 during normal operation when the mechanical needle valve 12 is not closed completely.

The pressure sensors 10 in the oxygen branch 2, the shared gas branch 5 and the gas mixing branch 6 may perform pressure measurement on the gas circuits so as to avoid high pressure therein and improve system security. Moreover, the gas flow can be compensated according to the information obtained from the pressure sensors 10.

The one-way valves 11 in the oxygen branch 2 and the shared gas branch 5 may prevent backflow of the gas in the oxygen branch 5 and an equilibrium gas branch (i.e. the air branch and the nitrous oxide branch).

The above-described electronic flow monitor may have the following disadvantages: in addition to some flow control valves for the flow regulation, the on-off controllers 7 are also used in the oxygen branch 2, the air branch 4 and the nitrous oxide branch 3 for on-off control of the corresponding gas circuits. Those on-off controllers 7 may lead to high cost and complicated structure.

SUMMARY OF THIS DISCLOSURE

This disclosure provides electronic flow monitors that may have low cost and simple structure, methods for controlling the same and anesthesia machines using the same.

In one aspect, an electronic flow monitor can include a control module, an oxygen branch for delivering oxygen, an equilibrium gas branch for delivering equilibrium gas, and a gas mixing branch for mixing the oxygen and the equilibrium gas. The control module can meter an oxygen flow and an equilibrium gas flow through flow sensors. A first flow controller can be disposed in the oxygen branch and a second flow controller can be disposed in the equilibrium gas branch. The first flow controller can regulate the gas flow in the oxygen branch between zero and a maximum value, and the second flow controller can regulate the gas flow in the equilibrium gas branch between zero and a maximum value. Both the first flow controller and the second flow controller can communicate with the control module through signals.

In some embodiments, a first on-off controller can be disposed in the gas mixing branch for on-off control of the gas mixing branch. The first on-off controller can communicate with the control module through signals.

In some embodiments, the gas mixing branch can be disposed with a mechanical flow meter for metering the gas flow in the gas mixing branch.

In some embodiments, the electronic flow monitor may include a plurality of equilibrium gas branches, where each of the equilibrium gas branches may be respectively disposed with a second flow controller.

In some embodiments, the equilibrium gas branches may have one shared gas branch, where an input of the shared gas branch can be connected with respective outputs of the equilibrium gas branches, and an output of the shared gas branch can be connected with an input of the gas mixing branch.

In some embodiments, the shared gas branch may be disposed with a second flow sensor in communication with the control module through signals. The control module can meter the equilibrium gas flow through the second flow sensor.

In some embodiments, a first flow sensor communicated with the control module through signals can be disposed in the oxygen branch.

In some embodiments, the electronic flow monitor can also include an oxygen bypass for bypassing the first flow controller.

In another aspect, an anesthesia machine can include the above-described electronic flow monitor.

In still another aspect, a method for controlling an electronic flow monitor may include:

receiving preset parameters including oxygen concentration, total flow and equilibrium gas type;

obtaining preset flows of oxygen and equilibrium gas based on the preset parameters; and respectively controlling actual flows of the oxygen and the equilibrium gas by a first flow controller and a second flow controller such that the actual flows and the preset flows are consistent.

This disclosure may provide one or more of the following advantages: the first flow controller and the second flow controller may not only implement on-off control of the gas circuits but also implement flow regulation for the gas circuits, thereby decreasing the number of the on-off controllers used while realizing simplified structure and lowered cost.

DETAILED DESCRIPTION

This disclosure is described below in detail with reference to specific implementations and figures.

Figure 1:
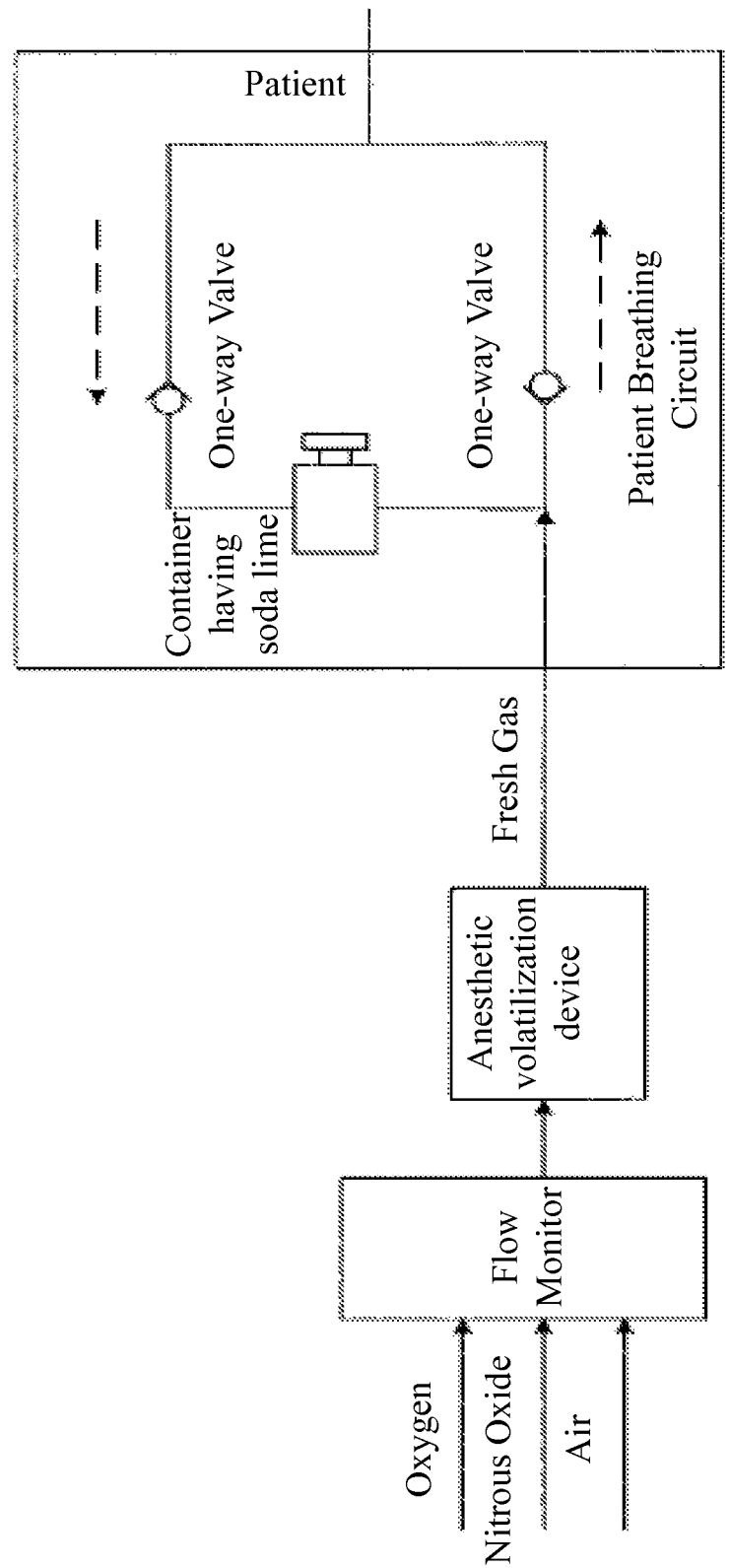
FIG. 1 is a structure diagram illustrating how fresh gas can be formed in an existing anesthesia machine.
Figure 2:
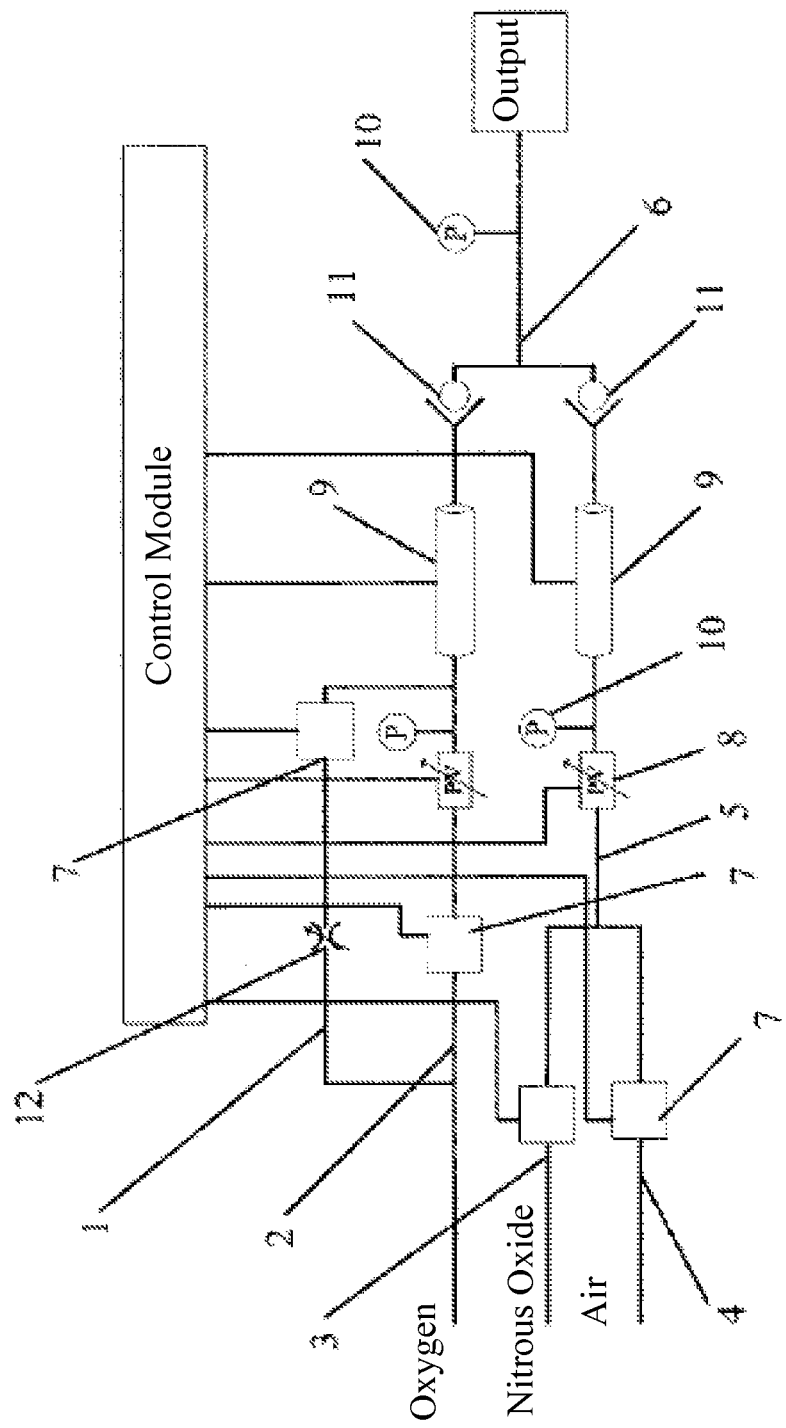
FIG. 2 is a structure diagram for an existing electronic flow monitor.
Figure 3:
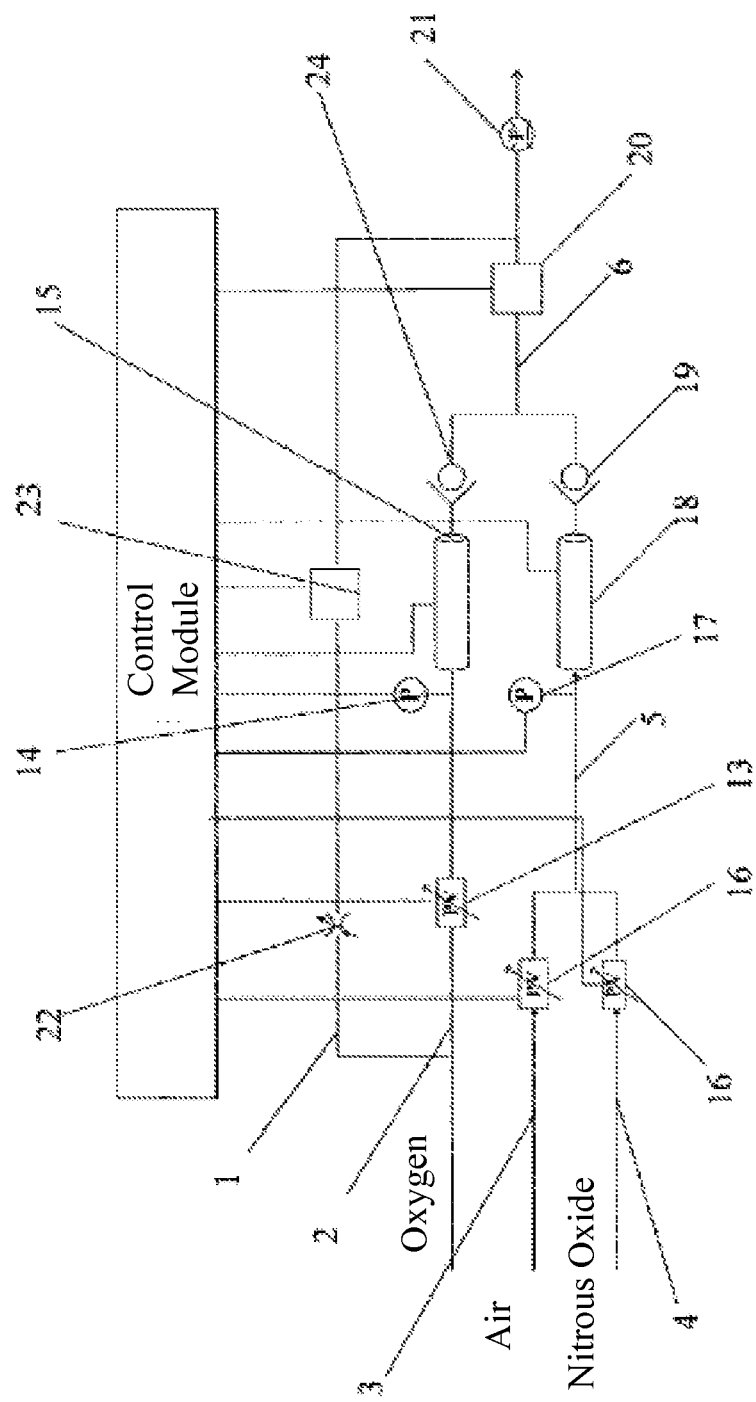
FIG. 3 is a structure diagram for an electronic flow monitor in accordance with an embodiment of this disclosure.
Figure 4:
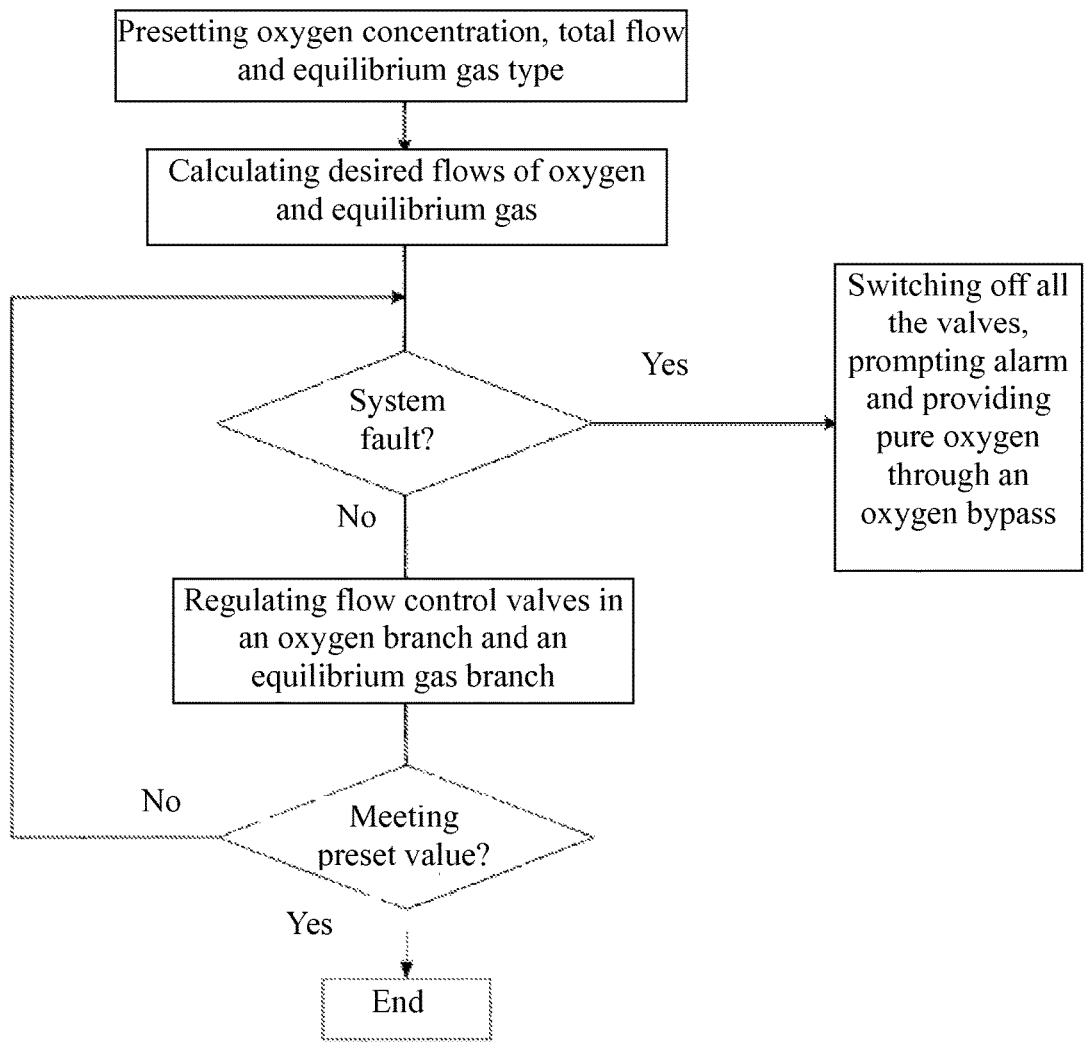
FIG. 4 is a flow chart for a method of controlling an electronic flow monitor in accordance with an embodiment of this disclosure.

As shown in FIGS. 3 and 4, an electronic flow monitor can include an oxygen branch 2, a nitrous oxide branch 4, an air branch 3, a gas mixing branch 6 and a control module. The oxygen branch 2 can provide pure oxygen. The nitrous oxide branch 4 and the air branch 3 can selectively provide air or nitrous oxide as equilibrium gas under the control of the control module. The gas mixing branch 6 can mix the oxygen with the equilibrium gas and output the mixed gas thereafter. The control module can also regulate an oxygen flow and an equilibrium gas flow so as to ensure the outputted gas to meet preset oxygen concentration and total flow.

The oxygen branch 2 can be disposed with a first flow controller 13, a first pressure sensor 14, a first flow sensor 15 and a first one-way valve 24. The first flow sensor 15 can be located downstream of the first flow controller 13; that is, the oxygen may flow through the first flow controller 13 and the first flow sensor 15 sequentially. The first flow controller 13 may realize both on-off control of the oxygen branch and flow regulation of the oxygen. The first pressure sensor 14 can perform pressure measurements and prevent the oxygen branch 2 from having too high pressure. The first flow sensor 15 can perform flow measurements and prevent the oxygen branch 2 from experiencing too large flow. The first one-way valve 24 can prevent backflow of the oxygen.

The air branch 3 and the nitrous oxide branch 4 may have a shared gas branch 5. The air branch 3 and the nitrous oxide branch 4 can each include a second flow controller 16, where the second flow controllers 16 can not only implement on-off control of the gas circuits but also achieve flow regulation for the gas circuits. It is noted that at most one of the air branch 3 and the nitrous oxide branch 4 can be opened by the corresponding second flow controller 16 at any given time.

The shared gas branch 5 may be disposed with a second pressure sensor 17, a second flow sensor 18 and a second one-way valve 19. The second pressure sensor 17 can perform pressure measurements and prevent the shared gas branch 5 from experiencing too high pressure, while the second pressure sensor 17 can also make compensation on flow values measured by the second flow sensor 18. The second flow sensor 18 can perform flow measurements and prevent the shared gas branch 5 from having too large flow. The second one-way valve 19 can prevent backflow of the equilibrium gas.

The gas mixing branch 6 can be disposed with a first on-off controller 20 and a mechanical flow meter 21 for gas flow metering. In order to improve system security, the first on-off controller 20 can cut off the connection between the respective branches and an output of the electronic flow monitor if any of the first flow controller 13 and the second flow controllers 16 has malfunction. For example, when the nitrous oxide branch 4 cannot be switched off by the second flow controller 16, there can be too much nitrous oxide that may cause damages to a patient. At this point, the nitrous oxide can be stopped from being outputted by closing the first on-off controller 20 in the gas mixing branch 6. Besides, the mechanical flow meter 21 can still display the gas flow in the gas mixing branch 6 in case there is no power supply.

The control module may communicate with the respective flow controllers, the respective flow sensors and the respective pressure sensors through signals. The control module can realize human-machine interaction, which by way of example can be used for setting oxygen concentration, total flow and equilibrium gas type (e.g., selecting air or nitrous oxide as the equilibrium gas). The control module can control the first flow controller 13, the second flow controllers 16 and the first on-off controller 20, and it can sample information from the respective flow sensors, the respective pressure sensors, the respective flow controllers and the on-off controller. Furthermore, when a system error is detected, the control module can cut off the power supply to all the flow controllers and the on-off controller, and prompt alarm information.

The electronic flow monitor can also include an oxygen bypass 1 capable of bypassing the first flow controller 13 of the oxygen branch 2. When the control module cuts off the power supply to all the flow controllers and the on-off controller after detecting a system error, pure oxygen can be provided to the patient through the oxygen bypass 1. A mechanical needle valve 22 for gas flow regulation may be disposed in the oxygen bypass 1. A second on-off controller 23 may also be disposed in the oxygen bypass 1 for on-off control of this gas circuit. During normal operation, the second on-off controller 23 can avoid oxygen output through the oxygen bypass 1 due to incomplete closure of the mechanical needle valve 22. In the case of system fault, the second on-off controller 23 would be in an "on" state so that the oxygen bypass 1 is kept open, while the first on-off controller 20 would be closed. The system fault can be power down of the system, or some parameters measured exceeding preset ranges. For example, if a measured pressure exceeds a standard pressure range, the control module may open the second on-off controller 23 (i.e. set the second on-off controller 23 in an "on" state). Therefore, the second on-off controller 23 is closed during normal operation, but it is open in the case of system fault.

A method for controlling the electronic flow monitor can include some following steps. Oxygen concentration and total flow can be preset, and equilibrium gas type may be selected (e.g. selecting air or nitrous oxide as the equilibrium gas). The control module may then calculate desired flows of the oxygen and the equilibrium gas based on such preset parameters. Subsequently, it is judged whether there is system fault. If so, each branch may be switched off by the on-off controller and the flow controllers, while the pure oxygen can be provided through the oxygen bypass. In case there is no system fault, the control module may open the first on-off controller in the gas mixing branch, switch on and regulate the first flow controller and the second flow controller, and sample information from the respective pressure sensors and the respective flow sensors. In this way, a closed-loop control can be achieved until the gas outputted from the electronic flow monitor can reach the oxygen concentration and the total flow preset by the user.

The electronic flow monitor can include an oxygen branch 2, at least one equilibrium gas branch, a gas mixing branch 6 and a control module. The oxygen branch 2 may output oxygen and the equilibrium gas branch may output equilibrium gas, where the oxygen and the equilibrium gas can mix with each other in the gas mixing branch 6. This may be equivalent to: the oxygen branch 2 and the equilibrium gas branch can be connected in parallel before being in series connection with the gas mixing branch 6, and then the gas mixing branch 6 may output the mixed gas. The oxygen branch 2 and the equilibrium gas branch can each have a first flow controller 13 and a second flow controller(s) 16, where both the first and the second flow controllers 13 and 16 can implement on-off control and gas flow regulation of their corresponding branch. This may be equivalent to: the first flow controllers 13 can regulate the gas flow in the oxygen branch between zero and a maximum value, and the second flow controller(s) 16 can regulate the gas flow in the equilibrium gas branch between zero and a maximum value. The zero value means to switch off a corresponding branch, and a nonzero value may refer to switching on the branch. The first and the second flow controllers 13 and 16 can communicate with the control module through signals.

One or more equilibrium gas branches can be connected with the gas mixing branch 6. Here two connection modes can be adopted: the equilibrium gas branch(es) may be directly connected with the gas mixing branch 6, or the equilibrium gas branch(es) may connect with the gas mixing branch 6 through a shared gas branch 5. When there are multiple equilibrium gas branches, such two connection modes can be used in combination. Each of the multiple equilibrium gas branches can provide one kind of equilibrium gas. However, it is noted that at most one kind of equilibrium gas can be selected at any given time. The equilibrium gas can be air, nitrous oxide or any other gases capable of being mixing with the oxygen in an anesthesia machine. Flow control valve for both gas flow regulation and on-off control of the gas circuits can be employed for the first flow controller 13 and the second flow controller(s) 16.

The gas mixing branch 6 can be disposed with a first on-off controller 20 for switching off the gas mixing branch 6 if the oxygen branch 2 and/or the equilibrium gas branch(es) have/has malfunction. The first on-off controller 20 can be realized by those gate valves capable of achieving on-off control of a gas circuit, or by those flow control valves implementing both gas flow regulation and on-off control of a gas circuit, or by any other structures capable of controlling on and off states of a gas circuit. The gas mixing branch 6 may also have no on-off controller 20. Alternatively, a mechanical flow meter for gas flow metering may be disposed in the gas mixing branch 6, where the mechanical flow meter can display the gas flow in a power-down situation. Such flow meter can be a mechanical rotameter.

First flow sensor 15 in the oxygen branch 2 can be located upstream or downstream of the first flow controller 13. Second flow sensor 18 in the equilibrium gas branch(es) can be located in the downstream of the second flow controller(s) 16. For example, the second flow controller 16 is disposed in the nitrous oxide branch 4 or the air branch 3, while the second flow sensor 18 is disposed in the shared gas branch 5. However, the second flow sensor 18 in the equilibrium gas branch can also be located upstream of the second flow controller 16. In this case, the number of the second flow sensor 18 may be the same as that of the equilibrium gas branch. For example, when the respective equilibrium gas branch(es) is directly connected with the gas mixing branch 6, it/they can each include a second flow sensor 18.

The oxygen branch 2 and the equilibrium gas branch(es) can also each have a one-way valve for preventing backflow of gas Each of the oxygen branch 2, the equilibrium gas branch(es), the shared gas branch 5 and the gas mixing branch 6 can be equipped with a pressure sensor for performing pressure measurements on a corresponding gas circuit. There may be no pressure sensors in these branches, however.

The electronic flow monitor can have an oxygen bypass 1 for bypassing the first flow controller 13 in the oxygen branch 2. An output of the oxygen bypass 1 may be directly connected with the gas mixing branch 6. For instance, the output of the oxygen bypass 1 may be directly connected with an output of the gas mixing branch (i.e. an output of the electronic flow monitor). Alternatively, the output of the oxygen bypass 1 may be directly connected with the oxygen branch 2 in the downstream of the first flow controller 13, e.g. between the first flow controller 13 and the first flow sensor 15. The oxygen bypass 1 can be disposed with a second on-off controller 23 and a third flow controller. The second on-off controller 23 is in an "closed" state in the case there is no power supply and the third flow controller can be used for flow regulation. There may be no second on-off controller and/or no third flow controller, however.

The nitrous oxide branch 4 and the air branch 3 can be respectively disposed with a pressure/pressure-difference measurement apparatus downstream of their respective second flow controller 16. The pressure/pressure-difference measurement apparatus may detect whether there is gas leakage in each branch.

This disclosure is described above as detailed illustrations with reference to specific implementations, while this disclosure should not be limited to these illustrations. For those of ordinary skills in the art, various conclusions or equivalents may be made without departing from the concept of this disclosure, while such conclusions or equivalents should be deemed to be included within the scope of this disclosure.

The invention claimed is:

1. An electronic flow monitor, comprising:
a control module that meters an oxygen flow and an equilibrium gas flow through flow sensors;
an oxygen branch for delivering the oxygen flow;
a first flow controller disposed in the oxygen branch that regulates gas flow in the oxygen branch between zero and a maximum value;
an equilibrium gas branch for delivering the equilibrium gas flow;
a second flow controller disposed in the equilibrium gas branch that regulates gas flow in the equilibrium gas branch between zero and a maximum value;
a gas mixing branch for mixing the oxygen flow and the equilibrium gas flow;
a first on-off controller disposed on the gas mixing branch for on-off control of the gas mixing branch;
an oxygen bypass for bypassing the gas mixing branch; and
a second on-off controller disposed along the oxygen bypass for on-off control of the oxygen bypass,
wherein the first and second flow controllers and first and second on-off controllers are each communicatively coupled to the control module, and
wherein the control module causes the first and second on-off controllers to be in opposite states, such that, if a fault is detected, the first on-off controller is controlled to be in an off state and the second on-off controller is controlled to be in an on state.

2. The electronic flow monitor of claim 1, wherein the gas mixing branch is disposed with a mechanical flow meter for metering gas flow in the gas mixing branch.

3. The electronic flow monitor of claim 1, wherein comprising a plurality of second flow controllers, and each of the equilibrium gas branches is respectively disposed with one of the plurality of second flow controllers.

4. The electronic flow monitor of claim 1, wherein the equilibrium gas branches have one shared gas branch, wherein an input of the shared gas branch is connected with respective outputs of the equilibrium gas branches, and an output of the shared gas branch is connected with an input of the gas mixing branch.

5. The electronic flow monitor of claim 1, wherein the control module meters the equilibrium gas flow through the second flow sensor.

6. The electronic flow monitor of claim 1, wherein the oxygen branch is further disposed with a first flow sensor communicated with the control module through signals.

7. The electronic flow monitor of claim 5, wherein the oxygen branch is further disposed with a first flow sensor communicated with the control module through signals.

8. An anesthesia machine, comprising an electronic flow monitor, wherein the electronic flow monitor comprises:
a control module that meters an oxygen flow and an equilibrium gas flow through flow sensors;
an oxygen branch for delivering oxygen;
a first flow controller disposed in the oxygen branch that regulates gas flow in the oxygen branch between zero and a maximum value;
an equilibrium gas branch for delivering equilibrium gas;
a second flow controller disposed in the equilibrium gas branch that regulates gas flow in the equilibrium gas branch between zero and a maximum value;
a gas mixing branch for mixing the oxygen and the equilibrium gas;
a first on-off controller disposed in the gas mixing branch for on-off control of the gas mixing branch;
an oxygen bypass for bypassing the gas mixing branch; and
a second on-off controller disposed in the oxygen bypass for on-off control of the oxygen bypass,
wherein the first and second flow controllers and first and second on-off controllers are each communicatively coupled to the control module, and
wherein the control module causes the first and second on-off controllers to be in opposite states, such that, if a fault is detected, the first on-off controller is controlled to be in an off state and the second on-off controller is controlled to be in an on state.

9. The anesthesia machine of claim 8, wherein the gas mixing branch is disposed with a mechanical flow meter for metering gas flow in the gas mixing branch.

10. The anesthesia machine of claim 8, wherein the electronic flow monitor comprises a plurality of equilibrium gas branches, and each of the equilibrium gas branches is respectively disposed with a second flow controller.

11. The anesthesia machine of claim 10, wherein the equilibrium gas branches have one shared gas branch, wherein an input of the shared gas branch is connected with respective outputs of the equilibrium gas branches, and an output of the shared gas branch is connected with an input of the gas mixing branch.

12. The anesthesia machine of claim 11, wherein the shared gas branch is disposed with a second flow sensor in communication with the control module through signals; the control module meters the equilibrium gas flow through the second flow sensor.

13. The anesthesia machine of claim 8, wherein the oxygen branch is further disposed with a first flow sensor communicated with the control module through signals.

14. A method for controlling an electronic flow monitor, wherein the electronic flow monitor comprises:
a control module that meters an oxygen flow and an equilibrium gas flow through flow sensors;
an oxygen branch for delivering oxygen;
a first flow controller disposed in the oxygen branch that regulates gas flow in the oxygen branch between zero and a maximum value;
an equilibrium gas branch for delivering equilibrium gas;
a second flow controller disposed in the equilibrium gas branch that regulates gas flow in the equilibrium gas branch between zero and a maximum value;
a gas mixing branch for mixing the oxygen and the equilibrium gas;
a first on-off controller disposed in the gas mixing branch for on-off control of the gas mixing branch;
an oxygen bypass for bypassing the gas mixing branch; and
a second on-off controller disposed in the oxygen bypass for on-off control of the oxygen bypass,
wherein the first and second flow controllers and first and second on-off controllers are each communicatively coupled to the control module, and
wherein the control module causes the first and second on-off controllers to be in opposite states, such that, if a fault is detected, the first on-off controller is controlled to be in an off state and the second on-off controller is controlled to be in an on state, wherein the method comprises:

receiving preset parameters including oxygen concentration, total flow and equilibrium gas type;

obtaining preset flows of oxygen and equilibrium gas based on the preset parameters; and respectively controlling actual flows of the oxygen and the equilibrium gas by the first flow controller and the second flow controller such that the actual flows and the preset flows are consistent.

15. The method of claim 14, wherein after obtaining the set flows of the oxygen and the equilibrium gas, the method further comprises:

controlling the actual flows of the oxygen and the equilibrium gas by the first flow controller and the second flow controller when there is no system fault.

16. The method of claim 15, wherein the gas mixing branch is disposed with a mechanical flow meter for metering gas flow in the gas mixing branch.

17. The method of claim 15, wherein the equilibrium gas branch includes a plurality of equilibrium gas branches and the second flow controller includes a plurality of second flow controllers, and each of the plurality of equilibrium gas branches includes one of the plurality of second flow controllers.

18. The method of claim 17, wherein the equilibrium gas branches have one shared gas branch, wherein an input of the shared gas branch is connected with respective outputs of the equilibrium gas branches, and an output of the shared gas branch is connected with an input of the gas mixing branch.

* * * * *